United States Patent [19]

Hawkins

[11] Patent Number: 4,971,959

[45] Date of Patent: Nov. 20, 1990

[54] TRISUBSTITUTED PHENYL ANALOGS HAVING ACTIVITY FOR CONGESTIVE HEART FAILURE

[75] Inventor: Lynn D. Hawkins, Saline, Mich.

[73] Assignee: Warner-Lambert Company, Morris Plains, N.J.

[21] Appl. No.: 292,580

[22] Filed: Dec. 30, 1988

Related U.S. Application Data

[63] Continuation of Ser. No. 38,252, Apr. 14, 1987, abandoned.

[51] Int. Cl.$^5$ ............... C07C 247/10; C07C 255/32; C07C 255/50; A61K 31/275
[52] U.S. Cl. ............................... 514/150; 260/404.5; 514/520; 514/618; 514/620; 514/622; 552/10; 552/11; 558/57; 558/389; 558/390; 558/396; 558/410; 560/21; 560/43; 560/45; 560/55; 560/60
[58] Field of Search ............... 564/161, 171, 162, 165; 514/622, 150, 520; 558/410, 413, 390, 396, 389; 552/10

[56] References Cited

U.S. PATENT DOCUMENTS

| 4,012,495 | 3/1977 | Schmiechen et al. ............... 424/274 |
| 4,138,581 | 2/1979 | Minatoya et al. .................... 560/109 |
| 4,186,129 | 1/1980 | Huth et al. ........................... 548/186 |
| 4,193,926 | 3/1980 | Schmiechen et al. ............ 560/42 X |
| 4,308,278 | 12/1981 | Schneider et al. .............. 548/317 X |
| 4,431,814 | 2/1984 | Iwataki et al. ...................... 548/230 |
| 4,442,116 | 4/1984 | Iwataki et al. ................. 548/188 X |
| 4,810,716 | 3/1989 | Connor et al. ....................... 514/365 |

FOREIGN PATENT DOCUMENTS

| 746107 | 2/1970 | Belgium . |
| 0163270 | 12/1985 | European Pat. Off. . |
| 2655232 | 8/1977 | Fed. Rep. of Germany . |
| 3104435 | 11/1982 | Fed. Rep. of Germany . |
| 7309399 | 1/1974 | Netherlands . |

*Primary Examiner*—Joseph P. Brust
*Attorney, Agent, or Firm*—Joan Thierstein

[57] ABSTRACT

Novel trisubstituted phenyl analogs are now found to have activity as for the treatment of congestive heart failure.

11 Claims, No Drawings

TRISUBSTITUTED PHENYL ANALOGS HAVING ACTIVITY FOR CONGESTIVE HEART FAILURE

This a continuation of U.S. application Ser. No. 038,252, filed 4-14-87, now abandoned.

BACKGROUND OF THE INVENTION

The novel compounds of the present invention are analogs of phenyl ethers having activity as inhibitors of phosphodiesterase, and thus useful in the treatment of heart failure, hypertension, atherosclerosis, depression, inflammation, or bronchial constriction. A distinguishing feature of the present compounds is the combination of substituents now providing novel trisubstituted phenyl analogs having advantageous biological activity.

For example, European Applications No. EP 163270A (Derwent Abstract 85-304758/49) and No. EP 178381 (Derwent Abstract 86-028533/05 have among their disclosures a dilower alkoxyphenyl and dilower alkoxy radical. Such a radical does not make obvious a phenyl radical of the present invention having limits for combinations of substituents particularly, for example, with cycloalkyl. U.S. Pat. No. 4,138,581 teaches compounds having a dicarbonyl substituted phenyl radical but again such a radical does not make obvious the specific dioxysubstituted phenyl radical of the present invention.

Similarly, the teachings of NL 7309399 (Derwent Abstract No. 0662V/04), DT 2655232 (Derwent Abstract No. 42080Y/24), NL 7009390 (Derwent Abstract No. 05545S-B) and BE 746107Q (Derwent Abstract No. 59376R-B) have dioxy substituents on a phenyl radical but do not make obvious the compounds of the present invention having the specific definitions of substituents combined on the phenyl moiety of the present invention's compounds.

Numerous references disclose dioxy substituted phenyls having a heterocyclic moiety as a third substituent contrary to the present invention. See U.S. Pat. Nos. 4,186,129; 4,012,495; 4,193,926; 4,431,814; 4,442,116, and 4,308,278 as well as German Application No. 3,104,435.

SUMMARY OF THE INVENTION

The present invention is a compound of the formula (I)

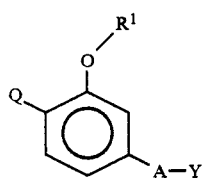

wherein $R^1$ is (a) branched alkyl of from four to seven carbons, optionally interrupted by O, S, or $NR^3$ wherein $R^3$ is hydrogen or lower alkyl, and optionally substituted by one of $NR^3R^4$ wherein $R^3$ is independently as defined above and $R^4$ is independently hydrogen or lower alkyl, $OR^3$ wherein $R^3$ is independently as defined above, halogen, trifluoromethyl, or $SR^3$ wherein $R^3$ is independently as defined above; or (b) cycloalkyl of three to six carbons;

Q is $XR^2$ wherein $R^2$ is lower alkyl and X is O or S; $NR^3R^4$ wherein $R^3$ and $R^4$ are independently as defined above; or $NO_2$;

A is a bond, straight or branched alkylenyl of from one to seven carbons or alkenylenyl of from two to six carbons having one, two, or three double bonds having the alkylenyl or the alkenylenyl optionally interrupted by O, S or $NR^3$;

Y is $CO_2R^5$ wherein $R^5$ is hydrogen, methyl or ethyl, $C(O)NR^3R^4$ wherein $R^3$ and $R^4$ are independently as defined above, CHO, $CH_2OH$, CN, $N_3$, $NO_2$ or $NR^3R^4$ wherein $R^3$ and $R^4$ are independently as defined above with the proviso that when $R^2$ is lower alkyl and A is alkenylenyl, then $R^1$ is cycloalkyl; and the pharmaceutically acceptable salts thereof.

The present invention is also a pharmaceutical composition for the treatment of heart failure, hypertension, atherosclerosis, depression, inflammation, or bronchial constriction comprising a cardiotonic, an antihypertensive, anticholesterol secretion, antidepressive, antiinflammatory, or antibronchial constriction effective amount or amount effective for treating heart failure of a compound of the formula I as defined above together with a pharmaceutically acceptable carrier.

The present invention is also a method of treating heart failure, hypertension, atherosclerosis, depression, bronchial constriction in a mammal, particularly human, suffering therefrom which comprises administering to said mammal a dosage form of a compound of the formula I.

A DETAILED DESCRIPTION OF THE INVENTION

In the compounds of formula I, the term "alkylenyl of from three to seven carbons" are straight or branched chain hydrocarbons of the noted number of carbons having two valances connecting two other moieties of the compound.

"Lower alkyl" is a hydrocarbon chain of from one to four carbons such as methyl, ethyl, propyl, or butyl and isomers thereof.

"Halogen" is fluoro, bromo, iodo, or chloro.

"Cycloalkyl" of from three to six carbons is cyclopropyl, cyclobutyl, cyclopentyl, or cyclohexyl.

"Alkenylenyl of from two to seven carbons having one, two, or three double bonds" is an unsaturated hydrocarbon chain, such as 1-propen-1-yl, 1-propen-2-yl, 1-buten-1-yl, 1-buten-2-yl, 1-buten-3-yl, and the like, and isomers thereof also having two valences connecting two other moieties of the compounds of formula I.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine tris(hydroxymethyl)aminomethane; and the like. (See for example, "Pharmaceutical Salts," *J. Pharm. Sci.* 66(1):1–19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom in the moiety denoted A above connecting the substituted phenyl and Y when A is a branched hydrocarbon and also may contain an asymmetric carbon in the definition of $R^1$ when defined as a branched chain hydrocarbon and/or optionally substituted. Thus, the invention includes the individual enantiomers, the pure S, the pure R isomer and mixtures thereof. The individual enantiomers may be prepared or isolated by methods known in the art.

Preferred embodiments of the present invention are compounds of formula I wherein Q is $XR^2$.

More preferred embodiments of the present invention are preferred compounds of formula I wherein $R^1$ is cyclopentyl.

Most preferred embodiments of the present invention are preferred embodiments of formula I wherein X is oxygen, $R^2$ is methyl, and Y is OH, $C(O)NH_2$, or $C(O)OR$.

More particularly, the compound of the present invention which is the most preferred is 3-(3-cyclopentoxy-4-methoxyphenyl)-n-propionate amide.

Generally, the compounds of formula I may be conveniently synthesized by initially reacting an appropriately substituted hydroxybenzaldehyde or hydroxybenzyl alcohol with an alkyl or alkenyl halide, as shown in Reaction Scheme 1, where $R^1$, $R^2$, and X are as defined above and Z is as defined below, followed by the addition of an appropriately functionalized side chain by the methodologies illustrated by four alternative pathways. The first alternative pathway is illustrated in Reaction Scheme 2. The second alternative pathway is illustrated in Reaction Scheme 3. The third alternative pathway is illustrated in Reaction Scheme 4. The fourth alternative pathway is illustrated in Reaction Scheme 5.

Reaction Scheme 1

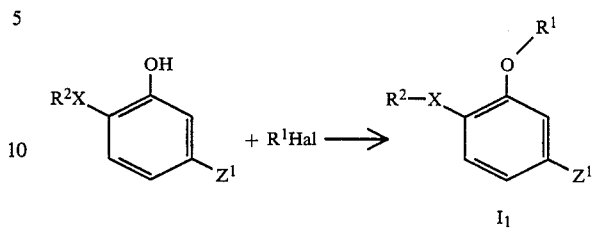

$Z^1$ is CHO or $CH_2OH$ $R^1$, $R^2$, X, and Hal are as described above

Reaction Scheme 2

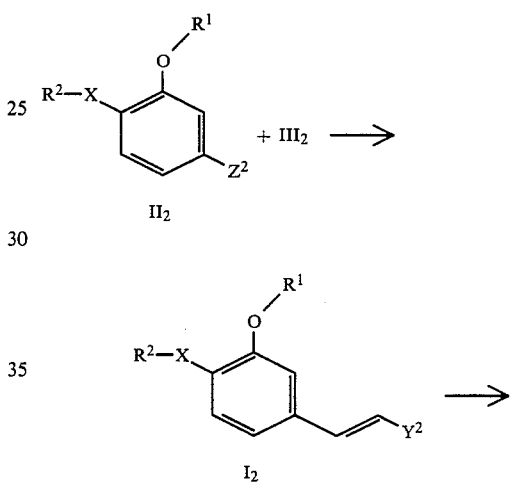

$Z^2$ is CHO $Y^2$ is $NO^2$, CN, $CO_2CH_3$ or $CO_2C_2H_5$ $R^1$, $R^2$, and X are described above Reaction Scheme 3

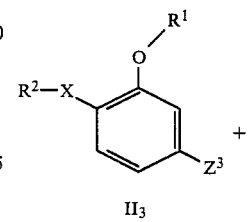

Reaction Scheme 5

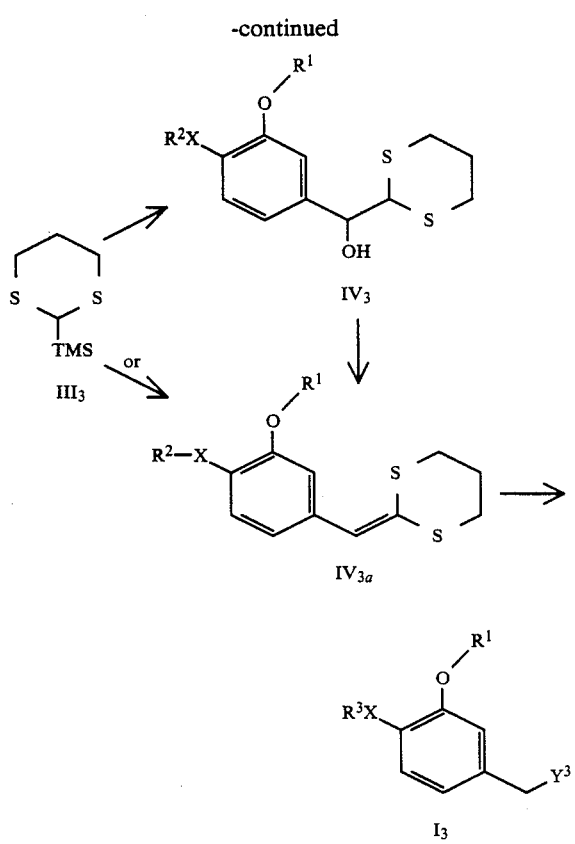

$Z^3$ is CHO
TMS is trimethylsilyl
$Y^3$ is $CO_2CH_3$, $CO_2C_2H_5$ or $CO_2H$
$R^1$, $R^2$, and X are described as above

Reaction Scheme 4

$Z^4$ is CHO
$X^4$ is $NHR^3$
$Y^4$ is $CO_2CH_5$ or $CO_2C_2H_5$
$U^4$ is N
$R^1$, $R^2$, $R^3$ and X are described above

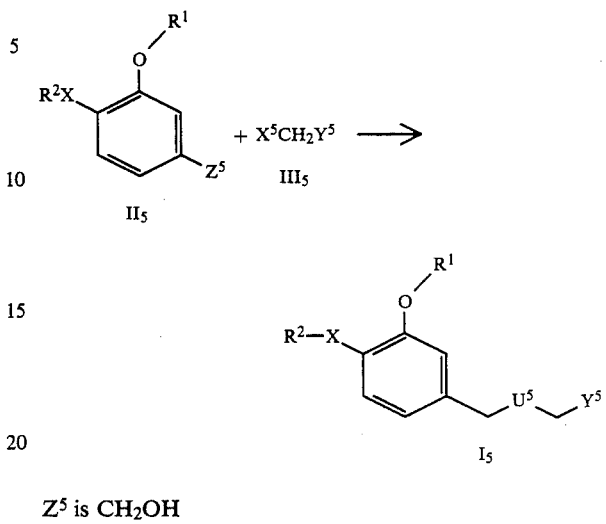

$Z^5$ is $CH_2OH$
$X^5$ is CL, Br, or I
$Y^5$ is $CO_2CH_3$ or $CO_2C_2H_5$
$R^1$, $R^2$ and X are described above
$U^5$ is O In Reaction Scheme 1, the process for preparing the claimed compounds of the formula $I^1$ wherein $R^1$ and $R^2$ are as defined above and Y is CHO or $CH_2OH$ (denoted as $Z^1$ in Scheme I), involves reacting a commercially available or readily prepared 3-hydroxybenzaldehyde or 3-hydroxybenzyl alcohol, substituted in the 4-position with substituents as disclosed for $XR_2$ above, with an alkyl or alkenyl halide in the presence of a small amount of halogen salt, such as NaI, KI or the like; preferably KI; base such as KOH, NaOH, $K_2CO_3$ and the like; preferably KOH, in an inert organic solvent such as methanol, ethanol, DMF (N,N-dimethylformamide), and the like or mixtures thereof, preferably ethanol. Temperatures of this reaction may be from room temperature to reflux temperature.

Another process for preparing the claimed compounds of formula $I_2$, wherein $R^1$ and $R^2$ are as defined above, and $Y^2$ is as defined below; uses the 3-alkoxy-4-substituted benzaldehyde (formula $I_1$, Reaction Scheme 1) as a starting material. This process is illustrated in Reaction Scheme 2. Condensation of the benzaldehyde with an appropriately functionalized alkyl group such as nitromethane, acetonitrile, trimethoxyphosphonoacetate, triethoxyphosphonoacetate, or the like (as depicted by the general formula $III_2$); with a base such as NaOH, KOH, NaH, KH, LDA (lithium diisopropyl amide), n-butyl lithium or the like, preferably NaH; in an inert solvent such as the methanol, ethanol, THF (tetrahydrofuran), DMF, HMPA (hexamethylphosphoramide), or the like or combinations thereof, preferably THF; provides compounds of general formula $I_2$. $R^1$ and $R^2$ in general formula $I_2$ are as defined above, $Y^2$ is defined as the functional groups $NO_2$, CN, $CO_2CH_3$ or $CO_2C_2H_5$. The predominant product of the process in Scheme 2 is a compound that is in the E-configuration, for example, greater than 90% of the yield. Reduction of the carbon-carbon double bond can be performed under hydrogenation conditions known to the trained artisan to provide the saturated compound of general formula $I_2^1$ wherein $R^1$, $R^2$, and $Y^2$ are as defined above.

Another process that can be used for synthesis of compounds of formula $I_3$ where X, $R^2$ and $R^1$ are as defined above and $Y^3$ is as defined below, is illustrated in Reaction Scheme 3. The synthesis is an "umpolung" condensation of the 3-alkoxy-4-substituted benzaldehyde of the general formula $I^1$, as defined in Reaction Scheme 1, with a properly functionalized alkyl group such as 1,3-dithiane, 2-trimethylsilyl- 1,3-dithiane, ethyl ethylthiomethylsulfoxide, bis(phenylthio)methane, or the like, preferably 2-trimethylsilyl-1,3-dithiane (formula $III_3$); in the presence of a base such as n-butyl lithium, LDA, potassium hexamethyldisilazene, or the like, preferably n-butyl lithium; in an inert solvent such as THF, ethyl ether, dioxane, HMPA, or the like, or combination thereof; preferably THF; under an inert atmosphere such as nitrogen or argon, and at a temperature between $-78°$ C. and $0°$ C. A ketene intermediate, formula $IV_{3a}$ wherein $R^1$, $R^2$, and X are as defined above, is formed in situ or upon elimination of $H_2O$ by the treatment of the condensed intermediate of the formula $IV_3$ with an acid such as TFA (trifluoroacetic acid), CSA (camphorsulfonic acid), p-TSA (para-toluene sulfonic acid), or the like, preferably TFA in an organic solvent such as dichloromethane, chloroform, benzene, toluene, or the like; at a reaction temperature between room temperature and reflux. The final product of general formula $I_3$ as defined above may be obtained by hydrolysis of the ketene intermediate of the formula $IV_{3a}$ wherein $R^1$, $R^2$, and X are defined above, in the presence of a desulfurizing reagent such as mercuric bromide, mercuric chloride, NBS (N-bromosuccinimide), NCS (N-chlorosuccinimide), or the like, preferably mercuric chloride; a buffering reagent such as mercuric oxide, cadmium carbonate, or the like, preferably mercuric oxide; in a protic solvent such as methanol, ethanol, water, or combinations thereof, preferably methanol; at a reaction temperature from room temperature to reflux. The hydrolysis product would provide compounds of general formula $I_3$ wherein $R^1$, $R^2$, and X are described above and $Y^3$ is $CO_2CH_3$, $CO_2C_2H_5$, or $CO_2H$.

Reaction Scheme 4 depicts another alternative process to obtain compounds of general formula $I_4$ where X, $R^1$, $R^2$, and $R^3$ are as defined above and $U^4$ and $Y^4$ are as defined below. The benzaldehyde of the formula $I^1$ defined above as a product in Reaction Scheme 1 may be condensed with the hydrochloride, hydrobromide or like salt, preferably the hydrochloride salt; of an ester of an amino acid such as depicted in formula $III_4$ wherein $X^4$ is $NHR^3$, $R^3$ is as described above, and $Y^4$ is $CO_2CH_3$ or $CO_2C_2H_5$. The condensation takes place in the presence of a buffering base such as sodium acetate, sodium bicarbonate, sodium carbonate, potassium bicarbonate, or the like, preferably sodium acetate; in an inert solvent such as methanol, ethanol, benzene, toluene, or the like or combinations thereof, preferably methanol; at a pH range from 4 to 6, at a temperature range from room temperature to reflux. The addition of a reducing reagent such as sodium cyanoborohydride, sodium borohydride, or the like, preferably sodium cyanoborohydride; provides the desired product of the general formula $I_4$ where $R^1$, $R^2$, $R^3$, and X are described above, $U^4$ is a nitrogen, and $Y^4$ is $CO_2CH_3$ or $CO_2C_2H_5$.

Reaction Scheme 5 depicts another alternative process to obtain compounds of general formula $I_5$ where X, $R^1$, and $R^2$ are as defined above and $U^5$ and $Y^5$ are as defined below. The benzyl alcohol from the formula $I^1$ in Reaction Scheme 1 may be deprotonated using a base such as NaOH, KOH, NaH, KH, LDA, n-butyl lithium or the like, preferably NaH; in an inert solvent such as methanol, ethanol, THF, DMF, HMPA, or the like, or combinations thereof, preferably DMF; followed by the addition of a compound defined as formula $III_5$ wherein $X^5$ is a halogen such as chlorine, bromine, or iodine, preferably bromine and $Y^5$ is $CO_2CH_3$ or $CO_2C_2H_5$. The reaction temperatures for this condensation may range from $0°$ C. to reflux. Products from this condensation are illustrated in general formula $I_5$ where $R^1$, $R^2$, and X are described above, $U^5$ is an oxygen, and $Y^5$ is $CO_2CH_3$ or $CO_2C_2H_5$.

The benzyl alcohol of the formula $I^1$ of Scheme 1 may be transformed to its benzaldehyde for use as starting materials in the alternative pathways to provide compounds of general formula I by oxidation processes known to the trained artisan. Likewise, the benzaldehyde described as a product in Reaction Scheme 1 may be transformed to the benzyl alcohol by reduction methodology known to the trained artisan to provide starting materials of Scheme 5.

Variations of reactions as defined in Schemes 2–5 are known to an ordinarily skilled artisan to provide chain extended compounds wherein A is a longer chain alkylenyl or alkenylenyl as defined above for general formula I. The functional groups, Y, in general formula I may be easily formed from compounds obtained from either Reaction Scheme 2, 3, 4 or 5 by reaction methodologies known to the ordinary artisan.

The starting materials for the preparation of the compounds of formula I of the present invention are commercially available, are known or can be prepared by methods known in the art.

Drying of reaction solvents are processes known to the trained artisan.

Separation and purification of the products of the described methods are by generally accepted processes known by an ordinarily skilled artisan.

The following examples further illustrate the invention and are not meant to be limiting.

EXAMPLES

EXAMPLE 1

3-Cyclopentoxy-4-methoxybenzaldehyde

To a solution of 54.9 g (0.36 mol) of 3-hydroxy-4-methoxybenzaldehyde in 400 mL of absolute ethanol was added 40.4 g (0.72 mol) of potassium hydroxide, 1.0 g (0.01 mol) of potassium iodide, and 77.0 mL (0.72 mol) of cyclopentyl bromide. The mixture was warmed to reflux for 48 hours at the end of which time the completed reaction was cooled to room temperature and concentrated to a syrup. The resulting residue was dissolved in 500 ml of ethyl acetate, washed with one, 100-mL portion of water, with one, 50-mL portion of dilute hydrochloric acid, with one, 100-mL portion of saturated sodium bicarbonate, and with one, 50-mL portion of saturated sodium chloride. The organic fraction was dried over sodium sulfate and concentrated to dryness. The amber syrup was liquid chromatographed over 500 g of silica gel using 20% ethyl ether in hexane as an eluent to provide the analytically pure oil upon drying in vacuo.

Yield: 74.4 g (0.34 mol) 93.6%

Calculated for $C_{13}H_{16}O_3$: C, 70.88%; H, 7.32%

Found: C, 71.15%; H, 7.20%.

EXAMPLE 2

3-Cyclopentoxy-4-nitrobenzaldehyde

Step 1. To a stirred suspension of 1.0 g (6.0 mmol) of 3-hydroxy-4-nitrobenzaldehyde in 50 mL of absolute ethanol was added 0.15 g (4.0 mmol) of sodium borohydride in small portions. The mixture was stirred for 15 minutes at the end of which time the orange solution was quenched with a slow, dropwise addition of excess glacial acetic acid. The resulting yellow solution was concentrated and azeotroped two times to dryness with 100-mL portions of toluene. The residue was dissolved in 50 mL of chloroform, washed two times with 25-mL portion of water, dried over magnesium sulfate and concentrated to dryness to an analytically pure yellow solid as 3-hydroxy-4-nitrobenzyl alcohol.

Yield: 0.94 g (5.6 mmol) 93%
mp: 94°-97° C.
Calculated for $C_7H_7NO_4$: C, 49.66%; H, 4.14%; N, 8.28%
Found: C, 49.33%; H, 4.07%; N, 8.20%.

Step 2. To a solution of 9.6 g (56.5 mmol) of 3-hydroxy-4-nitrobenzyl alcohol in 960 mL of dry N,N-dimethylformamide under a nitrogen atmosphere was added 11.7 g (83.6 mmol) of anhydrous potassium carbonate followed by 18.1 mL (169.0 mmol) of cyclopentyl bromide. The reaction mixture was warmed to 50° C. for 24 hours after which time the mixture was cooled to room temperature and concentrated to a dark brown residue under high vacuum. The residue was dissolved in 500 mL of chloroform, washed with two, 50 mL portions of saturated sodium chloride, dried over magnesium sulfate, and concentrated to dryness. Purification of the crude product with liquid chromatography over 200 g of silica gel and eluting with 10% methanol in chloroform provided the analytically pure 3-cyclopentoxy-4-nitrobenzyl alcohol upon drying in vacuo.

Yield: 11.0 g (46.5 mmol) 82.2%
mp: 54° C.
Calculated for $C_{12}H_{15}NO_4$: C, 60.70%; H, 6.32%; N, 5.90%
Found: C, 60.59%; H, 6.43%; N, 5.86%.

Step 3. To a stirred solution of 5.0 g (21.1 mmol) of 3-cyclopentoxy-4-nitrobenzyl alcohol in 200 mL of dry methylene chloride is added 19.0 g (218.5 mmol) of activated manganese dioxide in one portion. The brown suspension is warmed to reflux for 48 hours after which time the mixture is cooled to room temperature, filtered over Celite 545 and concentrated. Liquid chromatography over 200 g of silica gel eluting with 30% ethyl acetate in hexane provided the desired, analytically pure compound upon drying in vacuo.

Yield: 3.8 g (16.2 mmol) 76.6%
mp: 53°-54° C.
Calculated for $C_{12}H_{13}NO_4$: C, 61.21%; H, 5.53%; N, 5.95%
Found: C, 61.17%; H, 5.56%; N, 5.63%.

EXAMPLE 3

Methyl 3-(3-cyclopentoxy-4-methoxyphenyl)-E-propenoate

To a stirred suspension of 7.5 g (0.16 mol) of a 50% oil suspension of sodium hydride (previously washed with three, 10 mL portions of hexane) in 600 mL of dry tetrahydrofuran under a nitrogen atmosphere was added dropwise at room temperature 16.5 mL (0.10 mol) of trimethylphosphonoacetate in 100 mL of dry tetrahydrofuran over a 20 minute period. The white suspension was stirred for an additional 2 hours after which time 20.4 g (0.09 mol) of 3-cyclopentoxy-4-methoxybenzaldehyde in 150 mL of dry tetrahydrofuran was added dropwise over a 10 minute period. The final reaction mixture was stirred for an additional hour after which time the mixture was quenched with 75 mL of saturated sodium chloride. After separation of the solvent layers, the organic fraction was dried over sodium sulfate and concentrated. Liquid chromatography of the crude product over 250 g of silica gel with 20% ethyl acetate in hexane provided the desired, analytically pure product upon crystallization from hexane Yield: 22.0 g (0.08 mol) 74.3%
mp: 58°-59° C.
Calculated for $C_{16}H_{20}O_4$: C, 69.54%; H, 7.30%
Found: C, 69.32%; H, 7.17%. $H^1$-NMR (CDCl$_3$): δ1.55-2.05 (8H, m), 3.80 (3H, s), 3.88 (3H, s), 4.77-4.84 (1H, m), 6.30 (1H, d, J=16.0 Hz), 6.86 (1H, d, J=8.3 Hz), 7.07 (1H, s), 7.09 (1H, d, J=8.3 Hz), 7.64 (1H, d, J=16.0 Hz).

EXAMPLE 4

Methyl 3-(3-cyclopentoxy-4-nitrophenyl)-E-propenoate

To a stirred suspension of 0.89 g (22.3 mmol) of a 50% oil suspension of sodium hydride (previously washed with three, 10 mL portions of hexane) in 100 mL of dry tetrahydrofuran under a nitrogen atmosphere was added dropwise at room temperature 2.54 mL (15.7 mmol) of trimethylphosphonoacetate in 100 mL of dry tetrahydrofuran over a 30 minute period. The white suspension was stirred for an additional 10 minutes after which time 3.35 g (14.2 mmol) of 3-cyclopentoxy-4-nitrobenzaldehyde in 50 mL of dry tetrahydrofuran was added dropwise over a 20 minute period. The final reaction mixture was stirred for an additional hour after which time the mixture was quenched with excess saturated ammonium chloride. The mixture was extracted with three, 50 mL portions of methylene chloride and the combined organic fractions were washed with one, 50 mL portion of saturated sodium chloride, dried over magnesium sulfate and concentrated. Liquid chromatography of the crude product over 130 g of silica gel eluting with 50% ethyl acetate in hexane provided the desired, analytically pure solid.

Yield: 3.7 g (12.7 mmol) 89.4%
mp: 94°-95° C.
Calculated for $C_{15}H_{18}NO_5$: C, 61.83%; H, 5.84%; N, 4.81%
Found: C, 61.81%; H, 5.87%; N, 4.59%. $H^1$-NMR (CDCl$_3$): δ1.55-1.75 (2H, m), 1.77-2.02 (6H, m), 3.83 (3H, s), 4.93 (1H, m, 5 lines), 6.48 (1H, d, J=16.6 Hz), 7.13 (1H, d, J=8.3 Hz), 7.14 (1H, s), 7.43 (1H, d, J=16.6 Hz), 7.80 (1H, d, J=8.3 Hz).

EXAMPLE 5

Methyl 5-(3-cyclopentoxy-4-methoxyphenyl)-2,4-E,E-pentadienoate

To a stirred suspension of 0.26 g (5.41 mmol) of a 50% oil suspension of sodium hydride (previously washed with three, 10 mL portions of hexane) in 200 mL of dry tetrahydrofuran under a nitrogen atmosphere was added dropwise at room temperature 0.8 mL (4.94 mmol) of trimethylphosphonoacetate in 100 mL of dry tetrahydrofuran over a 20 minute period. The white suspension was stirred for an additional 16 hours after which time 0.99 g (4.02 mmol) of 3-(3-cyclopentoxy-4-methoxyphenyl)-E-propene-1-aldehyde in 30 mL of dry tetrahydrofuran was added dropwise over a 5 minute period. The final reaction mixture was stirred for an additional 30 minutes after which time the mixture was quenched with 50 mL of saturated ammonium chloride. After separation of the solvent layers, the organic fraction was extracted with 30 mL of ethyl acetate and the combined organic fractions were dried over sodium sulfate and concentrated. Crystallization from hexane provided the desired, analytically pure product.

Crystallizing solvent: Hexane
Yield: 81.4%
mp: 109°–112° C.
Calculated for $C_{18}H_{22}O_4$: C, 71.50%; H, 7.33%
Found: C, 71.39%; H, 7.65%. $H^1$-NMR (CDCl$_3$): δ1.55–1.75 (2H, m), 1.80–2.05 (6H, m), 3.77 (3H, s), 3.87 (3H, s), 4.75–4.85 (1H, m), 5.95 (1H, d, J=15.1 Hz), 6.72 (1H, dd, $J_1$=10.5 Hz, $J_2$=15.3 Hz), 6.7–6.8 (2H, m), 6.95–7.05 (2H, m), 7.44 (1H, dd, $J_1$=15.1 Hz, $J_2$=10.5 Hz).

EXAMPLE 6

Methyl 7-(3-cyclopentoxy-4-methoxyphenyl)-2,4,6-E-E-E-heptatrienoate

To a stirred suspension of 1.02 g (21.3 mmol) of a 50% oil suspension of sodium hydride (previously washed with three, 10 mL portions of hexane) in 150 mL of dry tetrahydrofuran under a nitrogen atmosphere was added dropwise at room temperature 2.3 mL (14.21 mmol) of trimethylphosphonoacetate in 50 mL of dry tetrahydrofuran over a 10 minute period. The white suspension was stirred for an additional 1.5 hours after which time 3.10 g (11.38 mmol) of 5-(3-cyclopentoxy-4-methoxyphenyl)-2,4-E,E-pentyldiene-1-aldehyde in 75 mL of dry tetrahydrofuran was added dropwise over a 15 minute period. The final reaction mixture was stirred for an additional 15 minutes after which time the mixture was quenched with 50 mL of saturated sodium chloride. The mixture was extracted with two, 50 mL portions of ethyl acetate and the combined organic fractions were dried over sodium sulfate and concentrated Liquid chromatography of the crude product over 200 g of silica gel with 10% ethyl acetate in hexane provided the desired, analytically pure yellow oil.

Yield: 2.35 g (7.16 mmol) 62.9%
Calculated for $C_{20}H_{24}O_4$: C, 73.14%; H, 7.37%
Found: C, 73.13%; H, 7.32%. $H^1$-NMR (CDCl$_3$): δ1.6–2.05 (8H, m), 3.77 (3H, s), 3.87 (3H, s), 4.7–4.9 (1H, m), 5.90 (1H, d, J=15.2 Hz), 6.3–6.5 (1H, m), 6.6–6.8 (2H, m), 6.84 (1H, d, J=8.9 Hz), 6.96–7.02 (2H, m), 7.36 (1H, d, J=15.3 Hz), 7.42 (1H, d, J=15.3 Hz).

EXAMPLE 7

Methyl 9-(3-cyclopentoxy-4-methoxyphenyl)-2,4,6,8-E,E,E,E-nonatetraenoate

To a stirred suspension of 0.13 g (2.71 mmol) of a 50% oil suspension of sodium hydride (previously washed with three, 3 mL portions of hexane) in 50 mL of dry tetrahydrofuran under a nitrogen atmosphere was added dropwise at room temperature 0.33 mL (2.04 mmol) of trimethylphosphonoacetate in 20 mL of dry tetrahydrofuran over a 5 minute period. The white suspension was stirred for an additional 2 hours after which time 0.40 g (1.34 mmol) of 7-(3-cyclopentoxy-4-methoxyphenyl)-2,4,6-E,E,E-heptatriene-1-aldehyde in 20 mL of dry tetrahydrofuran was added dropwise over a 5 minute period. The final reaction mixture was stirred for an additional 2 hours after which time the mixture was quenched with 50 mL of saturated sodium chloride. The mixture was extracted with three, 50 mL portions of ethyl acetate and the combined organic fractions were washed with 50 mL of saturated sodium chloride, dried over sodium sulfate and concentrated. Liquid chromatography of the crude product over 100 g of silica gel eluting with 10% ethyl acetate in hexane provided the desired, analytically pure yellow oil.

Yield: 0.41 g (1.16 mmol) 86.3%
Calculated for $C_{22}H_{26}O_4$: C, 74.55%; H, 7.39%
Found: C, 74.26%; H, 7.36%. $H^1$-NMR (CDCl$_3$): δ1.50–2.05 (8H, m), 3.76 (3H, s), 3.86 (3H, s), 4.7–4.9 (1H, m), 5.88 (1H, d, J=15.1 Hz), 6.2–7.1 (8H, m), 7.3–7.5 (2H, m).

EXAMPLE 8

Methyl 3-(4-amino-3-cyclopentoxyphenyl)-E-propenoate hydrochloride

To a stirred solution of 2.1 g (7.2 mmol) of methyl 3-(3-cyclopentoxy-4-nitrophenyl)-E-propenoate in 30 mL of methanol was added 6.3 mL (110.1 mmol) of glacial acetic acid and 2.0 g (35.8 mmol) of iron filings. The mixture was warmed to reflux and stirred for 16 hours after which time it was cooled to room temperature, filtered over Celite 545, and concentrated. Liquid chromatography over 200 g of silica gel using 50% ethyl acetate in hexane provided a pure oil. The product was dissolved in anhydrous ethyl ether, subjected to a stream of anhydrous hydrogen chloride gas upon which time an analytically pure, hydrochloride solid formed. The desired solid was collected, washed several times with anhydrous ethyl ether, and dried in vacuo.

Yield: 1.4 g (4.7 mmol) 66%
mp: 140°–142° C.
Calculated for $C_{15}H_{19}NO_3 \cdot 1.05$ HCl C, 60.49%; H, 6.72%; N, 4.70%; Cl, 12.43%
Found: C, 60.19%; H, 6.82%; N, 4.57%; Cl, 12.51%. $H^1$-NMR (CDCl$_3$): δ1.50–2.10 (8H, m), 3.82 (1H, s), 4.8–4.95 (1H, m), 6.42 (1H, d, J=16.1 Hz), 7.06 (1H, s), 7.09 (1H, d, J=7.9 Hz), 7.64 (1H, d, J=16.1 Hz), 7.72 (1H, d, J=7.9 Hz), 10.1–10.5 (1H, broad s).

EXAMPLE 9

Methyl 3-(3-cyclopentoxy-4-methoxyphenyl)-n-propionate

To a solution of 2.0 g (7.2 mmol) of methyl 3-(3-cyclopentoxy-4-methoxyphenyl)-E-propenoate in 100 mL of methanol is added 0.5 g of 5% palladium on carbon black. The suspension is shaken under a 50 psi atmosphere of hydrogen for 1.5 hours after which time the excess gas is dissociated and the solution is filtered over Celite 545. The mixture is concentrated to dryness followed by liquid chromatography of the crude product over 100 g of silica gel eluting with 15% ethyl acetate in hexane.

The final product is dried in vacuo and is found to be as analytically pure as an oil.
Yield: 1.69 g (6.1 mmol) 83.9%
Calculated for $C_{16}H_{22}O_4$: C, 69.04%; H, 7.97%

Found: C, 69.27%; H, 7.96%.

EXAMPLE 10

Methyl 5-(3-cyclopentoxy-4-methoxyphenyl)-n-pentanoate

To a solution of 0.20 g (0.66 mmol) of methyl 5-(3-cyclopentoxy-4-methoxyphenyl)-2,4-E,E-pentadienoate 75 mL of methanol is added 0.05 g of 5% palladium on carbon black. The suspension is shaken under a 50 psi atmosphere of hydrogen for 52 minutes after which time the excess gas is dissociated and the solution is filtered over Celite 545. The mixture is concentrated to dryness followed by liquid chromatography of the crude product over 100 g of silica gel eluting with 7.5% ethyl acetate in hexane. The final product is dried in vacuo and is found to be as analytically pure as an oil.

Yield 0.18 g (0.59 mmol) 88.8%
Calculated for $C_{18}H_{26}O_4$: C, 70.56%; H, 8.55%
Found C, 70.60%; H, 8.52%.

EXAMPLE 11

Methyl 7-(3-cyclopentoxy-4-methoxyphenyl)-n-heptanoate

To a solution of 0.52 g (1.58 mmol) of methyl 7-(3-cyclopentoxy-4-methoxyphenyl)-2,4,6-E,E,E-heptatrienoate in 100 mL of methanol is added 0.05 g of 5% palladium on carbon black. The suspension is shaken under a 50 psi atmosphere of hydrogen for 16 hours after which time the excess gas is dissociated and the solution is filtered over Celite 545. The mixture is concentrated to dryness followed by liquid chromatography of the crude product over 100 g of silica gel eluting with 7.5% ethyl acetate in hexane. The final product is dried in vacuo and is found to be as analytically pure as an oil.

Yield: 0.47 g (1.41 mmol) 89.0%
Calculated for $C_{20}H_{30}O_4$: C, 71.84%; H, 9.04%
Found: C, 71.58%; H, 9.04%.

EXAMPLE 12

Methyl 9-(3-cyclopentoxy-4-methoxyphenyl)-n-nonanoate

To a solution of 0.22 g (0.62 mmol) of methyl 9-(3-cyclopentoxy-4-methoxyphenyl)-2,4,6,8-E,E,E,E-nontetraenoate in 75 mL of methanol is added 0.05 g of 5% palladium on carbon black. The suspension is shaken under a 50 psi atmosphere of hydrogen for 20.9 hours after which time the excess gas is dissociated and the solution is filtered over Celite 545. The mixture is concentrated to dryness followed by liquid chromatography of the crude product over 100 g of silica gel eluting with 5% ethyl acetate in hexane. The final product is dried in vacuo and is found to be analytically pure as an oil.

Yield: 0.15 g (0.41 mmol) 66.7%
Calculated for $C_{22}H_{34}O_4$: C, 72.89%; H, 9.45%
Found: C, 73.09%; H, 9.58%.

EXAMPLE 13

3-(3-Cyclopentoxy-4-methoxyphenyl)-n-propanoic acid

To a stirring solution of 0.38 g (1.37 mmol) of methyl 3-(3-cyclopentoxy-4-methoxyphenyl)-n-propanoate in 20 mL of methanol was added dropwise 25 mL of a 1.0 N solution of potassium hydroxide in water over a 5 minute period. The mixture precipitated immediately, but returned to a solution after a 16 hour period at which time the solution was concentrated, diluted with 20 mL of water and neutralized to pH 1.0 with concentrated hydrochloric acid. The analytically pure white solid which formed was collected, washed several times with cold water, and dried in vacuo.

Yield: 0.33 g (1.25 mmol) 91.2%
mp: 114°–116° C.
Calculated for $C_{15}H_{20}O_4$: C, 68.16%; H, 7.63%
Found: C, 67.95%; H, 7.65%.

EXAMPLE 14

3-(3-Cyclopentoxy-4-methoxyphenyl)-E-propenoic acid

To a stirring solution of 0.8 g (2.9 mmol) of methyl 3-(3-cyclopentoxy-4-methoxyphenyl)-E-propenoate in 20 mL of methanol was added dropwise 25 mL of a 1.0 N solution of potassium hydroxide in water over a 5 minute period. The mixture precipitated immediately, but returned to a solution after a 16-hour period at which time the solution was concentrated, diluted with 20 mL of water and neutralized to pH 1.0 with concentrated hydrochloric acid. The analytically pure white solid which formed was collected, washed several times with cold water, and dried in vacuo.

Yield: 0.39 g (1.49 mmol) 51.3%
mp: 191°–193° C.
Calculated for $C_{15}H_{18}O_4$: C, 68.68%; H, 6.92%
Found: C, 68.46%; H, 6.93%.

EXAMPLE 15

3-(3-Cyclopentoxy-4-methoxyphenyl)-E-propenyl amide

A solution of 1.94 g (7.02 mmol) of methyl 3-(3-cyclopentoxy-4-methoxyphenyl)-E-propenoate in 100 mL of methanolic ammonia is placed in a pressure bomb. The reaction is warmed to 100° C. for 16 hours after which time it is cooled to room temperature and concentrated. Crystallization from ethyl acetate provides an analytically pure solid upon drying in vacuo.

Yield: 0.53 g (2.03 mmol) 23%
mp: 187°–191° C.
Calculated for $C_{15}H_{19}NO_3$: C, 68.94%; H, 7.33%; N, 5.36%
Found: C, 68.67%; H, 7.43%; N, 5.31%.

EXAMPLE 16

3-(3-Cyclopentoxy-4-methoxyphenyl)-n-propionyl amide

A solution of 0.46 g (1.65 mmol) of methyl 3-(3-cyclopentoxy-4-methoxyphenyl)-n-propionate in 100 mL of anhydrous methanolic ammonia is placed in a pressure bomb. The reaction is warmed to 100° C. for 24 hours after which time it is cooled to room temperature and concentrated. Crystallizing from 50% ethyl acetate in hexane provides an analytically pure solid upon drying in vacuo.

Yield: 0.14 g (0.53 mmol) 32.0%
mp: 126°–127.5° C.
Calculated for $C_{15}H_{21}NO_3$: C, 68.41%; H, 8.04%; N, 5.32%
Found: C, 68.25%; H, 7.78%; N, 5.31%.

EXAMPLE 17

3-(3-Cyclopentoxy-4-methoxyphenyl)-n-propionyl methylamide

To a solution of 0.35 g (1.26 mmol) of methyl 3-(3-cyclopentoxy-4-methoxyphenyl)-n-propionate in 50 mL of methanol is added 10 mL of anhydrous methylamine in a pressure bomb. The reaction is warmed to 100° C. for 25.5 hours after which time it is cooled to room temperature and concentrated. Liquid chromatography of the crude product over 100 g of silica gel eluting with ethyl acetate provides an analytically pure solid upon drying in vacuo.

Yield: 0.21 g (0.76 mmol) 60.1%
mp: 99°–101° C.
Calculated for $C_{16}H_{23}NO_3$: C, 69.28%; H, 8.36%; N, 5.05%
Found: C, 69.27%; H, 8.37%; N, 5.44%.

EXAMPLE 18

3-(3-Cyclopentoxy-4-methoxyphenyl)-n-propionyl ethylamide

To a solution of 0.35 g (1.26 mmol) of methyl 3-(3-cyclopentoxy-4-methoxyphenyl)-n-propionate in 50 mL of methanol is added 10 mL of anhydrous ethylamine in a pressure bomb. The reaction is warmed to 100° C. for 24 hours after which time it is cooled to room temperature and concentrated. Liquid chromatography of the crude product over 100 g of silica gel eluting with 10% hexane in ethyl acetate provides an analytically pure solid upon drying in vacuo.

Yield: 0.36 g (1.24 mmol) 98.1%
mp: 90.5°–92° C.
Calculated (with 0.1 equivalents of hexane) for $C_{17}H_{25}NO_3 \cdot 0.1 \, C_6H_{14}$ C, 70.46%; H, 8.87%; N, 4.67%
Found: C, 70.62%; H, 8.76%; N, 4.81%.

EXAMPLE 19

3-(3-Cyclopentoxy-4-methoxyphenyl)-n-1-propanol

To a stirred solution of 1.9 g (6.8 mmol) of methyl 3-(3-cyclopentoxy-4-methoxyphenyl)-n-propionate in 70 mL of dry methylene chloride under a nitrogen atmosphere was added dropwise 14.0 mL (14.0 mmol) of a 1.0M solution of diisobutylaluminum hydride in toluene over a 10 minute period at room temperature. The mixture was stirred for 16 hours at the end of which time the solution was slowly poured over a stirring solution of 100 mL of saturated ammonium chloride. The resulting solution was stirred for 30 minutes during which time a gelatinous solid formed. Absorption of the solid on excess Celite 545 followed by filtration over a pad of Celite 545 and elution with three, 50 mL portions of chloroform provided a yellow suspension. Separation of the layers followed by washing the organic fraction with 100 mL of saturated sodium chloride, drying over magnesium sulfate and concentration gave a crude yellow product. Liquid chromatography over 100 g of silica gel eluting with 20% ethyl acetate in hexane provided the desired, analytically pure product after drying in vacuo.

Yield: 1.42 g (5.67 mmol) 83.1%
mp: 38°–40° C.
Calculated for $C_{15}H_{22}O_3$: C, 71.97%; H, 8.86%
Found: C, 71.79%; H, 8.74%.

EXAMPLE 20

3-(3-Cyclopentoxy-4-methoxyphenyl)propenyl alcohol

To a stirred solution of 0.50 g (1.81 mmol) of methyl 3-(3-cyclopentoxy-4-methoxyphenyl)-E-propenoate in 70 mL of dry methylene chloride under a nitrogen atmosphere was added dropwise 3.0 mL (3.0 mmol) of a 1.0M solution of diisobutylaluminum hydride in toluene over a 10 minute period at room temperature. The mixture was stirred for 30 minutes at the end of which time the solution was slowly poured over a stirring solution of 30 mL of saturated ammonium chloride. The resulting solution was stirred for 30 minutes during which time a gelatinous solid formed. Absorption of the solid on excess Celite 545 followed by filtration over a pad of Celite 545 and elution with three, 30 mL portions of chloroform provided a yellow suspension. Separation of the layers followed by washing the organic fraction with 30 mL of saturated sodium chloride, drying over magnesium sulfate and concentration gave a crude yellow product. Liquid chromatography over 100 g of silica gel eluting with 30% ethyl acetate in hexane provided the desired, analytically pure product after drying in vacuo.

Yield: 0.29 g (1.57 mmol) 86.8%
Calculated for $C_{15}H_{20}O_3$: C, 72.55%; H, 8.12%
Found: C, 72.27%; H, 7.93%.

EXAMPLE 21

3-(3-Cyclopentoxy-4-methoxyphenyl)-E-propene-1-aldehyde

To a stirred solution of 0.12 g (0.48 mmol) of 3-cyclopentoxy-4-methoxyphenyl-E-propenyl alcohol in 20 mL of dry methylene chloride was added 0.5 g (6.1 mmol) of activated manganese dioxide in one portion. After stirring the brown suspension at room temperature for 6 hours, the mixture was filtered over Celite 545, eluted with two, 30 mL portions of chloroform, and concentrated. Crystallization of the crude product from hexane provided the desired, analytically pure product upon drying in vacuo.

Yield: 0.11 g (0.45 mmol) 93.0%
mp: 76.5°–78° C.
Calculated for $C_{15}H_{18}O_3$: C, 73.15%; H, 7.37%
Found: C, 73.30%; H, 7.33%.

EXAMPLE 22

5-(3-Cyclopentoxy-4-methoxyphenyl)-2,4-E,E-pentadiene-1-aldehyde.

To a stirred solution of 4.74 g (14.19 mmol) of 3-cyclopentoxy-4-methoxyphenyl-2,4-E,E-pentadiene-1-alcohol in 100 mL of dry methylene chloride was added 10.4 g (119.6 mmol) of activated manganese dioxide in one portion. After stirring the brown suspension at room temperature for 16 hours, the mixture was filtered over Celite 545, eluted with two, 75 mL portions of chloroform, and concentrated. Liquid chromatography of the crude product over 200 g of silica gel eluting with chloroform provided the desired, analytically pure product upon drying in vacuo from chloroform.

Yield 3.22 g (11.82 mmol) 83.3%
Calculated (with 0.05 equivalents of chloroform) for $C_{17}H_{20}O_3 \cdot 0.05 CHCl_3$: C, 73.58%; H, 7.26%
Found: C, 73.65%; H, 7.15%.

EXAMPLE 23

7-(3-Cyclopentoxy-4-methoxyphenyl)-2,4,6-E,E,E-heptatriene-1-aldehyde.

To a stirred solution of 1.00 g (3.33 mmol) of 3-cyclopentoxy-4-methoxyphenyl-2,4,6-E,E,E-heptatriene-1-alcohol in 40 mL of dry methylene chloride was added 5.0 g (57.3 mmol) of activated manganese dioxide in one portion. After stirring the brown suspension at room temperature for 16 hours, the mixture was filtered over Celite 545, eluted with two, 50 mL portions of chloroform, and concentrated. Liquid chromatography of the crude product over 100 g of silica gel with 10% ethyl acetate provided the desired, analytically pure product upon drying in vacuo from chloroform.

Yield: 0.56 g (1.88 mmol) 56.4%

Calculated (with 0.025 equivalents of chloroform) for $C_{19}H_{22}O_3 \cdot 0.025 CHCL_3$: C, 75.85%; H, 7.36%

Found: C, 75.80%; H, 7.38%.

EXAMPLE 24

Methyl 2-(3-cyclopentoxy-4-methoxyphenyl)ethanoate

Step 1. To a stirred solution of 5.4 mL (28.5 mmol) of 2-trimethylsilyl-1,3-dithiane in 50 mL of dry tetrahydrofuran cooled to -78° C. under an argon atmosphere was added 9.2 mL (28.6 mmol) of a 3.1 M solution of n-butyl lithium dropwise over a five minute period. The reaction mixture was stirred at $-78°$ C. for 30 minutes, warmed to 0° C., stirred for 15 minutes, and cooled to $-78°$ C. 5.7 g (25.8 mmol) of 3-cyclopentoxy-4-methoxybenzaldehyde in 15 mL of dry tetrahydrofuran was added dropwise to the mixture over a 15 minute period at the end of which time the final mixture was slowly warmed to room temperature and stirred for 16 hours. The reaction mixture was quenched with 50 mL of saturated ammonium chloride, diluted with 100 mL of ethyl acetate, the layers were separated, and the organic fraction was washed with 50 mL of saturated sodium chloride. The resulting organic fraction was dried over sodium sulfate, concentrated and liquid chromatographed over 100 g of silica gel eluting with 10% ethyl acetate in hexane. The desired product was concentrated, dried in vacuo and used in the subsequent step.

Step 2. To a stirred solution of the appropriate dithioketene derivative obtained in Step 1 in 75 mL of absolute methanol and 50 mL of dry tetrahydrofuran was added 15.5 g (57.0 mmol) of mercuric chloride under a nitrogen atmosphere. The suspension was stirred at room temperature for 5 hours at the end of which time the mixture was filtered over a pad of Celite 545 eluting with three, 25 mL portions of absolute methanol. The resulting solution was concentrated, diluted with 100 mL of chloroform washed with one, 25 mL portion of saturated sodium bicarbonate, with one, 25 mL portion of saturated sodium chloride, dried over magnesium sulfate, and concentrated to dryness Liquid chromatography of the crude product over silica gel eluting with 7.5% ethyl acetate in hexane provided an analytically pure oil.

Overall
Yield: 6.32 g (23.9 mmol) 96.2%
Calculated for $C_{15}H_{20}O_4$: C, 68.16%; H, 7.63%
Found: C, 68.30%; H, 7.61%.

EXAMPLE 25

Methyl 4-(3-cyclopentoxy-4-methoxyphenyl)-3-E-butenoate

Step 1. To a stirred solution of 0.87 mL (4.58 mmol) of 2-trimethylsilyl-1,3-dithiane in 50 mL of dry tetrahydrofuran cooled to -78° C. under an argon atmosphere was added 1.45 mL (4.51 mmol) of a 3.1 M solution of n-butyl lithium dropwise over a five minute period. The reaction mixture was stirred at $-78°$ C. for 30 minutes, warmed to 0° C., stirred for 20 minutes, and cooled to $-78°$ C. 1.03 g (4.18 mmol) of 3-(3-cyclopentoxy-4-methoxyphenyl)-E-propen-1-aldehyde in 12 mL of dry tetrahydrofuran was added dropwise to the mixture over a five minute period at the end of which time the final mixture was slowly warmed to room temperature and stirred for 16 hours. The reaction mixture was quenched with 30 mL of saturated ammonium chloride, diluted with 100 mL of ethyl acetate, the layers were separated, and the organic fraction was washed with 50 mL of saturated sodium chloride. The resulting organic fraction was dried over sodium sulfate, concentrated and liquid chromatographed over 100 g of silica gel eluting with 10% ethyl acetate in hexane. The desired product was concentrated, dried in vacuo and used in the subsequent step.

Step 2. To a stirred solution of the appropriate dithioketene derivative, obtained in Step 1, in 50 mL of absolute methanol and 25 mL of dry tetrahydrofuran was added 1.6 g (6.0 mmol) of mercuric chloride under a nitrogen atmosphere. The suspension was stirred at room temperature for 16 hours at the end of which time the mixture was filtered over a pad of Celite 545 eluting with three, 25 mL portions of absolute methanol. The resulting solution was concentrated, diluted with 100 mL of chloroform washed with one, 25 mL portion of saturated sodium bicarbonate, with one, 25 mL portion of saturated sodium chloride, dried over magnesium sulfate, and concentrated to dryness. Liquid chromatography of the crude product over silica gel eluting with 5% ethyl acetate in hexane provided an analytically pure oil.

Overall Yield: 0.45 g (1.55 mmol) 33.5%
Calculated for $C_{17}H_{22}O_4$: C, 70.32%; H, 7.64%
Found: C, 70.04%; H, 7.80%.
$H^1$-NMR (CDCl$_3$): $\delta$1.55–2.05 (8H, m), 3.24 (2H, dd, $J_1$=1.2 Hz, $J_2$=7.0 Hz), 3.72 (3H, s), 3.84 (3H, s), 4.75–4.85 (1H, m), 6.13 (1H, dt, $J_1$=7.0 Hz, $J_2$=15.8 Hz), 6.43 (1H, d, J=15.8 Hz), 6.20–6.95 (3H, m).

EXAMPLE 26

Methyl 4-(3-cyclopentoxy-4-methoxyphenyl)-2-E-butenoate

To a stirred solution of 2.1 mL (13.2 mmol) of trimethoxyphosphonoacetate in 60 mL of dry tetrahydrofuran at $-78°$ C. under an argon atmosphere was added dropwise 4.0 mL (12.4 mmol) of a 3.1 M solution of n-butyl lithium in hexanes over a 5 minute period. The mixture was stirred at $-78°$ C. for 10 minutes at the end of which time 3.16 g (12.0 mmol) of methyl 2-(3-cyclopentoxy-4-methoxyphenyl) ethanoate in 10 mL of dry tetrahydrofuran was added dropwise over a 5 minute period. After stirring the resulting solution for an additional 5 minutes, 12.0 mL (12.0 mmol) of a 1.0 M solution of diisobutylaluminum hydride in toluene was added dropwise over a 10 minute period followed by stirring at $-78°$ C. for 30 minutes and at room temperature for 1 hour. The resulting reaction mixture was quenched with 50 mL of saturated ammonium chloride and 50 mL of saturated sodium chloride and extracted with three, 50 mL portions of ethyl acetate. The combined organic fractions were dried over sodium sulfate and concentrated to dryness. Liquid chromatography of the crude product using 10% ethyl acetate in hexane as an eluent provided an analytically pure oil.

Yield: 0.47 g (1.62 mmol) 13.5% (69.5% recovered starting material)

Calculated (with 0.03 equivalents of chloroform) for $C_{17}H_{22}O_4$: C, 69.59%; H, 7.56%

Found: C, 69.68%; H, 7.63%. $H^1$-NMR (CDCl$_3$): $\delta$1.55–1.97 (8H, m), 3.76 (3H, s), 3.83 (3H, s), 3.94 (2H, dd, $J_1=1.6$ Hz, $J_2=7.5$ Hz), 4.70–4.95 (1H, m), 5.85 (1H, dt, $J_1=1.6$ Hz, $J_2=11.4$ Hz), 6.37 (1H, dt, $J_1=7.5$ Hz, $J_2=11.4$ Hz), 6.70–6.85 (3H, m).

EXAMPLE 27

3-(3-Cyclopentoxy-4-methoxyphenyl)-1-propyl aldehyde

To a solution of 1.31 g (5.23 mmol) of 3-(3-cyclopentoxy-4-methoxyphenyl)-E-propenyl-1-aldehyde is added 30 mg of 5% palladium on carbon black in a pressure bomb. The mixture is shaken under a 50 psi atmosphere of hydrogen at room temperature for 4.3 hours after which time the mixture is depressurized, filtered over Celite 545 and concentrated to dryness. Purification using liquid chromatography over 100 g of silica gel eluting with 10% ethyl acetate in hexane provides an analytically pure oil upon drying in vacuo from chloroform.

Yield: 0.10 g (0.40 mmol) 10.9%

Calculated (with 0.025 equivalents of chloroform) for $C_{15}H_{20}O_3.0.025$ CHCl$_3$:

C, 71.81%; H, 8.03%

Found: C, 71.75%; H, 7.93%.

EXAMPLE 28

3-(3-Cyclopentoxy-4-methoxyphenyl)-1-O-p-toluene sulfonyl propanol

To a stirred solution of 1.31 g (5.23 mmol) of 3-(3-cyclopentoxy-4-methoxyphenyl)-1-propanol in 30 mL of dry triethylamine with a catalytic amount of 4-N,N-dimethylaminopyridine was added 2.2 g (11.7 mmol) of p-toluenesulfonyl chloride in one portion. The reaction mixture was stirred at room temperature for 48 hours at the end of which time the mixture was poured over 50 mL of cold water. The aqueous suspension was extracted with three, 30 mL portions of chloroform and the combined organic fractions were dried over magnesium sulfate and concentrated to dryness. Liquid chromatography of the crude syrup over 100 g of silica gel eluting with 10% ethyl acetate in hexane provided the desired tosylate as an oil.

Yield: 0.77 g (1.90 mmol) 36.3%

Calculated for $C_{22}H_{28}O_5S$: C, 65.33%; H, 6.98%

Found: C, 65.04%; H, 7.01%.

EXAMPLE 29

3-(3-Cyclopentoxy-4-methoxyphenyl)-1-propyl azide

To a stirred solution of 0.21 g (0.5 mmol) of 3-(3-cyclopentoxy-4-methoxyphenyl)-1-O-p-toluenesulfonyl-1-propanol in 10 mL of dry N,N-dimethylformamide under a nitrogen atmosphere was added 0.7 g (1.0 mmol) of sodium azide and 0.6 g (0.4 mmol) of potassium iodide in single portions. The mixture was stirred at room temperature for 16 hours at the end of which time the reaction was quenched with excess water and extracted with three, 25 mL portions of chloroform. The combined organic fractions were dried over magnesium sulfate and concentrated under high vacuum to dryness. The resulting oil was purified to an analytically pure oil using liquid chromatography over 50 g of silica gel and eluting with 10% ethyl acetate in hexane followed by drying in vacuo.

Yield: 0.14 g (0.51 mmol) 94.2%

Calculated for $C_{15}H_{21}N_3O_2$: C, 65.43%; H, 7.69%; N, 15.26%

Found: C, 65.37%; H, 7.44%; N, 15.05%.

EXAMPLE 30

3-(3-Cyclopentoxy-4-methoxyphenyl)-1-propyl nitrile

To a stirred solution of 0.22 g (0.5 mmol) of 3-(3-cyclopentoxy-4-methoxyphenyl)-1-O-p-toluenesulfonyl-1-propanol in 10 mL of dry acetone was added 0.7 g (1.0 mmol) of potassium cyanide and 0.3 g (0.2 mmol) of potassium iodide in single portions. The mixture was warmed to reflux for 48 hours after which time the solution was concentrated to dryness. The residue was dissolved in 50 mL of chloroform, washed with 20 mL of water, dried over magnesium sulfate, and concentrated to dryness. Liquid chromatography of the crude product over 50 g of silica gel eluting with 10% ethyl acetate in hexane provided an analytically pure oil upon drying in vacuo from chloroform.

Yield: 0.05 g (0.19 mmol) 37.1%

Calculated (with 0.01 equivalents of chloroform) for $C_{16}H_{21}NO_2.0.01$ CHCl$_3$: C, 73.82%; H, 8.13%; N, 5.38%

Found: C, 73.76%; H, 7.91%; N, 5.21%.

EXAMPLE 31

3-(3-Cyclopentoxy-4-methoxyphenyl)-1-propyl bromide

To a stirred solution of 3.3 g (13.2 mmol) of -(3-cyclopentoxy-4-methoxyphenyl)-1-propanol in 75 mL of dry methylene chloride at 0° C. under a nitrogen atmosphere was added 4.3 g (16.4 mmol) of triphenylphosphine followed by a slow, portionwise addition of N-bromosuccinimide over a 5 minute period. The reaction mixture was stirred at 0° C. for 1.5 hours at the end of which time the mixture was quenched with excess methanol and stirred for an additional 10 minutes. Concentration of the mixture to dryness followed by liquid chromatography purification using 200 g of silica gel and elution 50% chloroform in hexane provided an analytically pure oil upon drying in vacuo.

Yield: 4.17 g (13.0 mmol) 98.6%

Calculated for $C_{15}H_{21}BrO_2$: C, 57.52%; H, 6.76%; Br, 25.51%

Found: C, 57.48%; H, 6.75%; Br, 25.20%.

EXAMPLE 32

1-n-Butyl-3-cyclopentoxy-4-methoxybenzene

To a stirred solution of 0.9 g (2.9 mmol) of 3-(3-cyclopentoxy-4-methoxyphenyl)-1-bromo-n-propane in 70 mL of dry tetrahydrofuran under a nitrogen atmosphere at room temperature was added dropwise 8.0 mL (21.6 mmol) of a 2.7 M solution of methyl magnesium chloride in tetrahydrofuran over a 5 minute period. The reaction mixture was warmed to reflux for 48 hours at the end of which time the mixture was cooled to room temperature and slowly quenched with excess saturated ammonium chloride. The aqueous suspension was extracted with three, 50 mL portions of ethyl acetate and the combined organic fractions were washed with saturated sodium chloride, dried over sodium sulfate, and concentrated to dryness. Liquid chromatography of the crude product over 100 g of silica gel using 10% ethyl ether in hexane provided an analytically pure oil upon drying in vacuo with a chloroform azeotrope.

Yield: 0.57 g (2.30 mmol) 78.9%

Calculated (with 0.04 equivalents of chloroform) for $C_{16}H_{24}O_2.0.04\ CHCl_3$: C, 76.10%; H, 9.57%

Found: C, 76.03%; H, 9.45%.

EXAMPLE 33

1-Amino-3-(3-cyclopentoxy-4-methoxyphenyl)-n-propane

A solution of 1.82 g (5.81 mmol) of 3-(3-cyclopentoxy-4-methoxyphenyl)-1-bromo-n-propane in 100 mL of methanolic ammonia is placed in a pressure bomb and warmed to 80° C. for 9 hours. The mixture is cooled to room temperature and concentrated to dryness. Crystallization of the crude solid with 5% ethanol in ethyl acetate provides an analytically pure solid as the hydrobromide salt.

Yield: 0.96 g (3.85 mmol) 66.3%

Calculated for $C_{15}H_{23}NO_2.HBr.0.5\ H_2O$: C, 53.10; H, 7.43; N, 4.13; Br, 23.55

Found: C, 53.16; H, 7.36; N, 4.17; Br, 23.66.

EXAMPLE 34

2-(3-Cyclopentoxy-4-methoxyphenyl)-1-nitro-E-ethylene

To a stirred solution of 1.02 g (4.63 mmol) of 3-cyclopentoxy-4-methoxybenzaldehyde in 20 mL of methanol was added 0.3 mL (5.5 mmol) of nitromethane followed by 0.2 g (5.0 mmol) of sodium hydroxide in 5 mL of water in single portions. The mixture was stirred for 4 hours after which time the decomposing mixture was concentrated, diluted with 20 mL of water and acidified to pH 1 with concentrated hydrochloric acid. The aqueous solution was extracted with three, 10 mL portions of chloroform and the combined organic fractions were dried over magnesium sulfate and concentrated. Liquid chromatography of the crude mixture over 100 g of silica gel eluting with 5% ethyl acetate in hexane provided an analytically pure solid.

Yield: 0.08 g (0.30 mmol) 6.6% (53.9% recovered starting material)

mp: 134°-136° C.

Calculated for $C_{14}H_{17}NO_4$: C, 63.86%; H, 6.51%; N, 5.32%

Found: C, 64.02%; H, 6.79%; N, 5.17%.

EXAMPLE 35

Methyl N-(3-cyclopentoxy-4-methoxybenzyl)glycine ester hydrochloride

To a stirred solution of 1.4 g (10.9 mmol) of methyl glycine ester in 50 mL of anhydrous methanol was added 0.8 g (9.5 mmol) of anhydrous sodium acetate in one portion. The mixture was refluxed for 16 hours after which time the mixture was cooled to room temperature and 1.0 g (4.5 mmol) of 3-cyclopentoxy-4-methoxybenzaldehyde in 5 mL of anhydrous methanol was added in one portion. The resulting mixture was stirred for an additional 2 hours after which time 0.2 g (3.2 mmol) of sodium cyanoborohydride was added in small portions over a 5 minute period. The resulting reaction mixture was stirred at room temperature for 2 hours followed by quenching with excess glacial acetic acid, concentration of the mixture, and azeotroping off the solvents three times to dryness with 50 mL portions of toluene. The crude product was crystallized from ethyl acetate to vive an analytically pure product as its hydrochloric salt.

Yield: 0.39 g (1.33 mmol) 29.3% mp: 154°-155° C.

Calculated for $C_{16}H_{23}NO_4.HCl$: C, 58.16%; H, 7.34%; N, 4.25%; Cl, 10.75%

Found: C, 58.17%; H, 7.34%; N, 4.21%; Cl, 10.97%.

EXAMPLE 36

3-Cyclopentoxy-4-methoxybenzyl alcohol

To a stirred solution of 10.42 g (47.3 mmol) of 3-cyclopentoxy-4-methoxybenzaldehyde in 100 mL of absolute ethanol was added 0.9 g (23.8 mmol) of sodium borohydride in one portion. The mixture was stirred for 1 hour at room temperature after which time the reaction was quenched with excess acetic acid, concentrated and azeotroped to dryness three times with 25 mL portions of toluene. The residue was dissolved in 100 mL of chloroform, washed with two, 25 mL portions of saturated sodium chloride, dried over magnesium sulfate, and concentrated to dryness. Liquid chromatography of the crude oil over 200 g of silica gel with 10% ethyl acetate in hexane provided an analytically pure oil after drying in vacuo.

Yield: 9.2 g (41.4 mmol) 87.5%

Calculated for $C_{13}H_{18}O_3$: C, 70.24%; H, 8.16%

Found: C, 70.36%; H, 8.15%.

EXAMPLE 37

2-O-(3-Cyclopentoxy-4-methoxybenzyl)-2-acetate methyl ester

To a stirred suspension of 0.7 g (13.6 mmol) of 50% sodium hydride (previously washed with three, 10 mL portions of hexane) in 5 mL of dry N,N-dimethylformamide at 0° C. under a nitrogen atmosphere was added dropwise 2.1 g (9.5 mmol) of 3-cyclopentoxy-4-methoxybenzyl alcohol in 10 mL of dry tetrahydrofuran over a 10 minute period. The mixture was stirred at 0° C. for 30 minutes at the end of which time 1.1 mL (22.2 mmol) of methyl bromoacetate was added in one portion. The resulting mixture was warmed to room temperature, stirred for 16 hours and then quenched with excess methanol. The mixture was concentrated under high vacuum, diluted with 100 mL of chloroform, washed with 50 mL of saturated sodium chloride, dried over magnesium sulfate, and concentrated to dryness. Liquid chromatography of the crude mixture over 200 g of silica gel eluting with 10% ethyl acetate in hexane provided the desired analytically pure product as an oil plus the starting benzyl alcohol after azeotroping to dry with chloroform.

Yield: 0.93 g (3.16 mmol) 33.1% desired (57.1% starting material)

Calculated (with 0.03 equivalents of chloroform) for $C_{16}H_{22}O_5.0.03\ CHCl_3$: C, 64.50%; H, 7.34%

Found: C, 64.23%; H, 7.45%.

The compounds of formula I have initially been found to be useful in a pharmacological assay for PDE III inhibition. The assay is an in vitro showing of selective inhibition of phosphodiesterase. Previously recognized PDE III inhibitors are known to possess cardiotonic activity as well as to inhibit platelet aggregation. Thus, activity of PDE III inhibition as shown by representative compounds of the formula I demonstrates utility of the present invention for compounds of formula I.

The protocol of the assays for the compounds of the present invention is generally as described by Thompson, et al. in *Advances in Cyclic Nucleotide Research*, Vol 10, edited by Brooker, Greengard and Robison: Raven Press, New York, 1979; having modifications as found in "Studies Aimed at Elucidating the Mechanism of Action of CI 914, A New Cardiotonic Agent", Weishaar, R. E., et al., *Eur. J. Pharmacol.*, 119 (1985) pp. 205-215.

The assays monitor the phosphodiesterase activity as inhibited in crude homogenate or in salt fractions containing partially purified forms of the enzyme from human platelet cells or J774 Macrophage tumor cells by compounds of the present invention. The inhibition is expressed as percent inhibition at $10^{-5}$M concentration. The inhibition of the enzymes by the examples indicated fall in the range of 8-45% toward the human platelet phosphodiesterase and 19-94% toward the J774 Macrophage phosphodiesterase. Both cell types, human platelet and J774 Macrophage, can be isolated by methods known to the trained artisan.

Further evidence is provided to show the compounds of formula I are useful for the treatment of congestive heart failure, coronary heart disease, myocardial ischemia, angina, and hypertension. Particularly, the compounds of the present invention are superior agents for the treatment of congestive heart failure.

That is, in generally accepted tests, representative compounds of the present invention are shown to cause significant increases in coronary blood flow in rats and also to produce substantial increases in contractility and decreases in blood pressure, without affecting heart rate. Thus, biological effects of the present invention compounds include beneficial effects similar to those observed for calcium antagonists.

The effects of increased coronary blood flow result from a complementary direct stimulatory effect on the myocardium as observed in a generally accepted test in isolated atrial tissue denoted below as CVIH. Particularly, initial direct stimulation by the compounds of the present invention provides additional support to a failing heart complementary to afterload reduction resulting from vasodilation. Such stimulation is also known as a positive inotropic effect.

TEST FOR INOTROPIC, CHRONOTROPIC, AND VASCULAR ACTIVITIES IN THE ISOLATED LANGENDORFF RAT HEART (CVIH)

Perfusion Technique

Male rats (400-600 gms) are pretreated with 2000 units Na heparin (Parke-Davis) and anesthetized with Na pentobarbital (50 mg/kg, Butler Co.) administered intraperitoneally. Once anesthetized, the rat heart is rapidly excised, the ascending aorta fitted to the aortic perfusion cannula, and secured with a ligature. The coronary arteries were perfused initially at a rate of about 15 ml/min for two to three minutes, after which they are perfused at constant pressure of 70 mm Hg and temperature of 37° C. The electrocardiogram (ECG) is recorded using two platinum electrodes positioned at the base and apex of the left ventricle. A second heart is excised, cannulated, and perfused by the same method outlined above. Both hearts are tested in parallel. The standard physiological salt solution (PSS) is a modified Krebs-Hanseleit bicarbonate buffer of the following composition in mM concentration: NaCl, 127; NaHCO$_3$, 25; dextrose, 5.5; Na Pyruvate, 2.0; KCl, 4.7; MgSO$_4$, 1.1; KH$_2$PO$_4$, 1.2; CaCl$_2$.2H$_2$O, 2.5; CaNa$_2$EDTA, 0.05.

A 30-minute stabilization period is observed before starting the test protocol.

Microprocessor Controlled Coronary Perfusion and Drug Delivery System

The microprocessor control system is a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing a solution at a specified drug concentration (DC) at rates proportional to total coronary flow (CF$_T$). Drug concentrations are increased by proportionate increases in the rate of DC infusion over CF$_T$ via the microprocessor keyboard The proportional flow rates for DC:CF$_T$ is about 0.0002 1 at the low end and 0.02:1 at the high end of the dose-response curve. Dose-response curves encompassing at least two log doses are carried out by preparing two DCs with a concentration difference of 1:100. Following the first dose range of two log doses, the DC is switched, proportional pumping rate adjusted, and the dose-response curve continued for another two log doses. The standard dose-response curve is carried out in one-half log dose increments starting at a subthreshold dose and ending at a dose which produces near maximal response in activity. Standard reference compounds are tested over the range of $10^{-9}$ to $10^{-6}$M.

Measurements

Measurements are for coronary flow (CF). Units are: CF, milliliters/minute (ml/min) CF is calculated by recording analog outputs from pumps 1 and 2. Outputs from pump #1=CF$_T$ and the output from pump #2=CF for heart B (CF$_B$). CF for heart A (CF$_A$) is calculated (CF$_T$−CF$_B$=CF$_A$).

Using the above coronary blood flow evaluation technique, the effects of the compounds of each indicated example is shown as the EC (effective concentration) 25/(effective concentration) EC 50.

The biological data from the above assays are summarized in the following Table A.

TABLE A

| In Vitro Langendorf Isolated Rat Heart | |
|---|---|
| Example No. | EC 25/EC 50 (Coronary Flow) |
| 3 | $2 \times 10^{-6}/>5 \times 10^{-4}$ M |
| 9 | $1.5 \times 10^{-5}/2.2 \times 10^{-5}$ |
| 13 | $4 \times 10^{-6}/1.5 \times 10^{-5}$ |
| 16 | $3 \times 10^{-6}/1 \times 10^{-5}$ |
| 19 | $2 \times 10^{-6}/7 \times 10^{-6}$ |
| 21 | $1.1 \times 10^{-6}/2 \times 10^{-6}$ |

Further, a representative compound demonstrates in a generally accepted in vivo assay for the compounds of formula I of the present invention effects on myocardial contractility, heart rate and coronary flow as follows:

TEST FOR IN VIVO MYOCARDIAL INOTROPIC ACTIVITY IN THE ANESTHETIZED DOG

Method

Adult mongrel dogs of either sex are anesthetized with pentobarbital, 35 mg/kg, IV, and are maintained under anesthesia with a continuous infusion of pentobarbital, 3.5 mg/kg/hr. The trachea is intubated, but the animals are permitted to breathe spontaneously. A cannula is inserted into the femoral vein for administering test agents. A Millar catheter tip pressure transducer or a fluid filled catheter is inserted into the ascending aorta via the femoral artery for measuring pressure. A Millar catheter tip pressure transducer is passed into the left ventricle via the left carotid artery for measuring left ventricular blood pressure. Needle electrodes are placed subcutaneously for recording a lead II electrocardiogram. Before administering test agents, control data is acquired over a period of at least thirty minutes.

The test agent is dissolved in dimethylacetamide. Each dose is administered in a volume of 0.5 ml over a period of one minute. Appropriate vehicle controls are also administered.

When tested by this protocol, representative compounds of formula I, when administered at a dose of 1 mg/kg, produced an increase in contractility, a minimal increase in blood pressure, and an increase in heart rate as shown in the following Table B.

TABLE B

In Vivo Myocardial Inotropic Activity in the Anesthetized Dog

| Example No. | Number Tested | Dosage (mg/kg) | Contract-ility* | Blood* Pressure | Heart* Rate |
|---|---|---|---|---|---|
| 3 | 1 | 1.0 | +77% | +16% | +20% |
| 9 | 1 | 1.0 | +36 | +5 | +41 |
| 13 | 4 | 1.0 | +47 | +9 | +23 |
| 16 | 6 | 1.0 | +127 | +5 | +25 |
| 19 | 1 | 1.0 | +91 | +9 | +25 |
| 21 | 2 | 1.0 | +62 | −1 | +35 |

*All values define a percent incrase ("+") or decrease ("−") from the control data, i.e., prior to dosing.

Accordingly, the present invention also includes a pharmaceutical composition for treating heart disease, such as congestive heart failure, hypertension, atherosclerosis, depression or bronchial constriction comprising a corresponding cardiotonic, antihypertension, antiatherosllerosis, antidepressant or anticonstriction effective amount of a compound of the formula I as defined above together with a pharmaceutically acceptable carrier.

The present invention further includes a method for treating hypertension, heart disease, particularly heart failure, atherosclerosis, depression, or bronchial constriction in mammals suffering therefrom comprising administering to such mammals either orally or parenterally a corresponding pharmaceutical composition containing a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. The powders may be prepared to be suitable for use as inhalants. In the tablet the active compound is mixed with carrier having the necessary binding properties in suitable proportions and compacted in the shape and size desired the powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methylcellulose, sodid carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents. Liquid form preparations may also be prepared to be suitable for use as an inhalant.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it may be preferred to maintain the unused portion of said liquid doses at low temperature (i.e., under refrigeration) in order to retard possible decomposition. The solid form preparations intended to be converted to liquid form my contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these in packaged form.

The quantity of active compound in a unit dose of preparation may be varied or adjusted from 25 mg to 500 mg preferably to 50 mg to 150 mg according to the particular application and the potency of the active ingredient. The compositions can, of desired, also contain other compatible therapeutic agents.

In therapeutic use as described above, the mammalian dosage range for a 70 kg subject is from 0.05 mg/kg to 25 mg/kg of body weight per day or preferably 0.5 mg/kg to 10 mg/kg of body weight per day. The dosages, however, may be varied depending upon the requirements of the patient the everity of the condition being treated, and the compound being employed. Determination of the proper dosage for a particular situation is within the skill of the art. Generally, treatment is initiated when appropriate with smaller dosages which are less than the optimum dose of the compound. Thereafter the dosage is increased by small increments until the optimum effect under the circumstances is reached. For convenience, the total daily dosage may by divided and administered in portions during the day if desired.

I claim:

1. A compound of the formula (I)

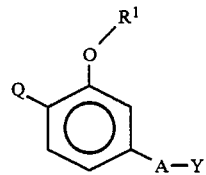

wherein R' is cycloalkyl of three to six carbons;
Q is $XR^2$ wherein $R_2$ is lower alkyl, and X is O and S;
A is a bond, straight or branched alkylenyl of from one to seven carbons or alkenylenyl of from two to six carbons having one, two or three double bonds having the alkylenyl or alkenylenyl, optionally interrupted by O, S, or $NR^5$;
wherein $R^5$ is hydrogen, methyl or ethyl;
Y is $C(O)NR_3R_4$ wherein $R_3$ and $R_4$ are independently hydrogen or lower alkyl, azido or CN.

2. A compound of claim 1 wherein $R^1$ is cyclopentyl or cyclohexyl.

3. A compound of claim 2 wherein $R^1$ is cyclopentyl.

4. A compound of claim 3 wherein the embodiment is 3-(3-cyclopentoxy-4-methoxyphenyl)-E-propenyl amide.

5. A compound of claim 3 wherein the embodiment is 3-(3-cyclopentoxy-4-methoxyphenyl)-n-propionyl amide.

6. A compound of claim 3 wherein the embodiment is 3-(3-cyclopentoxy-4-methoxyphenyl)-n-propionyl methylamide.

7. A compound of claim 3 wherein the embodiment is 3-(3-cyclopentoxy-4-methoxyphenyl)-n-propionyl ethylamide.

8. A compound of claim 3 wherein the embodiment is 3-(3-cyclopentoxy-4-methoxyphenyl)-1-propyl azide.

9. A compound of claim 3 wherein the embodiment is 3-(3-cyclopentoxy-4-methoxyphenyl)-1-propyl nitrile.

10. A pharmaceutical composition for treating cardiovascular disease comprising a cardiotonic or antihypertensive effective amount of a compound of formula I of claim 1 and a pharmacologically acceptable carrier.

11. A method for treating cardiovascular disease in a mammal suffering therefrom which comprises administering a compound of Formula I of claim 1 in unit dosage form to said mammal.

* * * * *